US010582999B2

(12) United States Patent
Kovacs (10) Patent No.: US 10,582,999 B2
(45) Date of Patent: Mar. 10, 2020

(54) SHOULDER JOINT SUPPORTING TISSUE REPLACEMENT SYSTEM (71) Applicant: Biomet Manufacturing, LLC, Warsaw, IN (US)

(72) Inventor: Michael Francis Kovacs, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 54 days.

(21) Appl. No.: 16/028,802

(22) Filed: Jul. 6, 2018

(65) Prior Publication Data

US 2019/0015193 A1    Jan. 17, 2019

Related U.S. Application Data (60) Provisional application No. 62/530,935, filed on Jul. 11, 2017.

(51) Int. Cl.
*A61F 2/40* (2006.01)
*A61F 2/08* (2006.01)
*A61F 2/30* (2006.01)

(52) U.S. Cl.
CPC .............. *A61F 2/08* (2013.01); *A61F 2/4014* (2013.01); *A61F 2/4081* (2013.01); *A61F 2002/30461* (2013.01); *A61F 2002/30462* (2013.01); *A61F 2002/30469* (2013.01); *A61F 2002/30578* (2013.01); *A61F 2002/4018* (2013.01)

(58) Field of Classification Search
CPC ................ A61F 2/08; A61F 2002/5093; A61F 2002/3241; A61F 2/36; A61F 2/34; A61F 2/32; A61F 2002/30461; A61F 2002/30474; A61F 2002/30462; A61F 2002/3822; A61F 2/40–4081; A61F 2002/4007–4096
See application file for complete search history.

(56) References Cited

U.S. PATENT DOCUMENTS 6,228,122 B1 * 5/2001 McGann ............. A61F 2/30742
623/23.11
2014/0330311 A1   11/2014 Denham et al.

* cited by examiner

*Primary Examiner* — Thomas Sweet
*Assistant Examiner* — Rebecca Lynee Zimmerman
(74) *Attorney, Agent, or Firm* — Schwegman Lundberg & Woessner, P.A.

(57) ABSTRACT

Various joint replacements are disclosed herein, as are methods of use thereof. The joint replacements can have a flexible band or multiple flexible bands that can link together a first part of the joint replacement and a second part of the joint replacement. The flexible band or bands can be tensioned to establish proper tension in the patient's joint. In certain circumstances, the joint replacement can be a shoulder joint replacement.

16 Claims, 6 Drawing Sheets

SHOULDER JOINT SUPPORTING TISSUE REPLACEMENT SYSTEM

CLAIM OF PRIORITY

This application claims the benefit of U.S. Provisional Patent Application Ser. No. 62/530,935, filed on Jul. 11, 2017, the benefit of priority of which is claimed hereby, and which is incorporated by reference herein in its entirety.

FIELD OF THE DISCLOSURE

The present disclosure relates to joint replacement systems, including joint replacements, instruments, and methods for installation thereof. Specifically, the present disclosure relates to shoulder replacement systems that incorporate features for replicating the support provided by natural ligaments in the shoulder.

BACKGROUND

A joint capsule is a watertight sac that surrounds a joint. In the shoulder, the joint capsule is formed by a group of ligaments that connect the humerus to the glenoid. These ligaments are the main source of stability for the shoulder. The ligaments include the superior, middle, and inferior glenohumeral ligaments, which help hold the shoulder in place and keep it from dislocating.

The shoulder also includes a rotator cuff, which is a group of tendons and muscles connecting the upper arm (humerus) to the shoulder blade (scapula). The rotator cuff tendons cover the shoulder joint and joint capsule and provide stability to the shoulder. The muscles allow the shoulder to rotate. The rotator cuff tendons also encircle the humeral head (ball) and help to keep the humeral head in the glenoid (socket) when the arm is elevated. These tendons also help to rotate the humerus on the glenoid so the arm can be raised. Without normal function of the rotator cuff, the humeral head may move upward out of the glenoid socket, which makes it difficult or impossible to raise the arm up. If a conventional joint replacement is used in this situation (i.e., where the rotator cuff is damaged or lacking), though there may be some pain relief, the humeral head usually remains upward out of the socket and elevation of the arm is impossible. Thus, a reverse shoulder replacement is typically indicated for situations such as this. A reverse shoulder replacement places an artificial ball where the normal glenoid socket is located, and an artificial socket where the normal humeral head is located. Reverse shoulder replacements can change the mechanics of the shoulder and enable the artificial joint to function when the rotator cuff is either absent or when there is significant bone loss.

The present disclosure provides shoulder replacements and methods that can be used to stabilize the replacement in instances where using a traditional shoulder replacement would be difficult.

SUMMARY

To better illustrate the system disclosed herein, a non-limiting list of examples is provided here:

Example 1 includes a joint replacement system comprising a glenoid component including a concave articulating surface and a peripheral surface, a humeral component including a convex head and a peripheral surface, and a first flexible band attached to the peripheral surfaces of the glenoid component and the humeral component, the first flexible band linking the glenoid component to the humeral component and providing tension therebetween.

In Example 2, the system of Example 1 can optionally further comprise a plurality of flexible bands attached to the peripheral surfaces of the glenoid component and the humeral component, the plurality of flexible bands linking the glenoid component to the humeral component and providing tension therebetween.

In Example 3, the system of Example 1 can optionally include wherein the first flexible band is composed of suture.

In Example 4, the system of any one of or any combination of Examples 1 and 3 can optionally further comprise a first opening on the peripheral surface of the glenoid component, wherein a portion of the first flexible band is inserted through the first opening to attach the first flexible band to the peripheral surface of the glenoid component.

In Example 5, the system of Example 4 can optionally further comprise a first opening on the peripheral surface of the humeral component, wherein a portion of the first flexible band is inserted through the first opening to attach the first flexible band to the peripheral surface of the humeral component.

In Example 6, the system of any one of or any combination of Examples 1-5 can optionally further comprise a second flexible band attached to the peripheral surfaces of the glenoid component and the humeral component, the second flexible band linking the glenoid component to the humeral component and providing tension therebetween, where the second flexible band is tensioned tighter than the first flexible band.

In Example 7, the system of any one of or any combination of Examples 1-6 can optionally further comprise a mesh linking the glenoid component to the humeral component.

In Example 8, the system of Example 7 can optionally include wherein the first flexible band is part of the mesh.

In example 9, the system of any one of or any combination of Examples 1-8 can optionally include wherein the first flexible band has a self-locking structure.

Example 10 includes a method of implanting a joint replacement comprising attaching a glenoid component to a patient's glenoid, attaching a humeral component to a patient's humerus, linking the glenoid component to the humeral component using a first flexible band, and tensioning the first flexible band to keep the patient's humeral component in registration with the glenoid component, In Example 11, the method of Example 10 can optionally further comprise linking the glenoid component to the humeral component using a plurality of flexible bands.

In Example 12, the method of Example 11 can optionally include wherein the plurality of flexible bands comprise a mesh that links the glenoid component to the humeral component.

In Example 13, the method of any one of or any combination of Examples 10-12 can optionally further comprise linking the glenoid component to the humeral component using a second flexible band, and tensioning the second flexible band to a greater degree of tension than the first flexible band.

In Example 14, the method of any one of or any combination of Examples 10-13 can optionally further comprise locking the first flexible band after tensioning the first flexible band.

In Example 15, the method of Example 14 can optionally include wherein the first flexible band comprises a self-locking mechanism, and the method further comprises self-locking the first flexible band after tensioning the first flexible band.

In Example 16, the method of Example 15 can optionally include wherein first flexible band is composed of suture, and the self-locking mechanism comprises a self-constricting passage formed in the suture.

In Example 17, the method of Example 16 can optionally further comprise passing a portion of the first flexible band through the self-constricting passage to form a loop of suture.

In Example 18, the method of Example 17 can optionally further comprise pulling on a free end of the first flexible band to decrease a size of the loop of suture, thereby causing the self-constricting passage to constrict about the portion of the first flexible band and lock the first flexible band within the self-constricting passage.

In Example 19, the method of any one of or any combination of Examples 10-18 can optionally further comprise attaching the first flexible band to a peripheral surface of the glenoid component and to a peripheral surface of the humeral component.

In Example 20, the method of any one of or any combination of Examples 10-19 can optionally further comprise passing a first portion of the first flexible band through a first opening of the glenoid component, and passing a second portion of the first flexible band through a first opening of the humeral component.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure any manner.

DETAILED DESCRIPTION

In describing the examples of the disclosure illustrated and to be described with respect to the drawings, specific terminology will be used for the sake of clarity. However, the disclosure is not intended to be limited to any specific terms used herein, and it is to be understood that each specific term includes all technical equivalents.

The present disclosure is directed at joint replacements having aspects that replicate natural tissue and/or ligaments. The joint replacements can be used in a traditional shoulder arthroplasty (TSA) or reverse shoulder arthroplasty (RSA) procedures.

Figure 1:
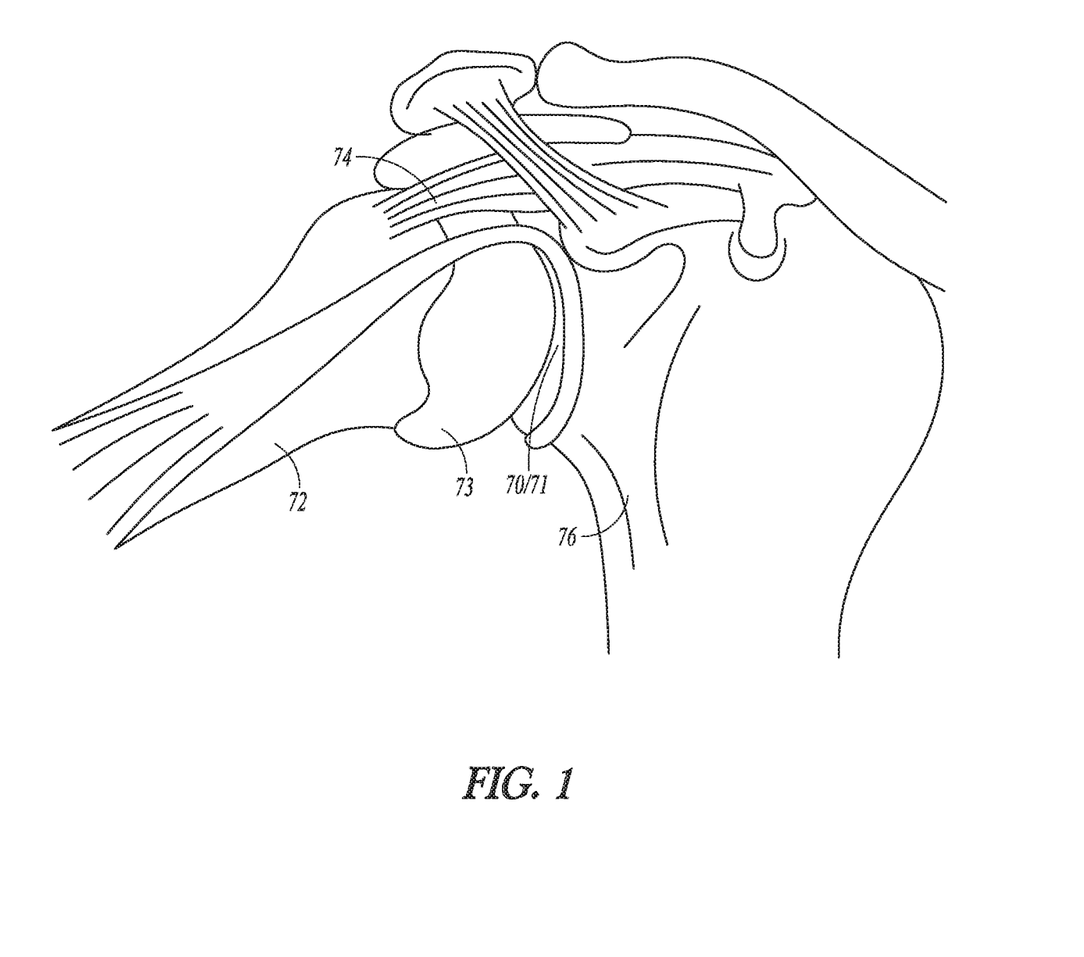
FIGS. 1-2 are anatomic views of a shoulder joint.

FIG. 1 illustrates a shoulder joint with several ligaments stripped away. As shown, the joint includes a humerus 72 and a scapula 76 that has a glenoid 70 with a socket 71 for interacting with a humeral head 73 of humerus 72. Humeral head 73 can articulate within socket 71 to allow for normal motion of the shoulder joint. A critical ligament for maintaining humeral head 72 within socket 71 is rotator cuff 74. As noted above, when rotator cuff 74 becomes damaged (e.g., torn or degraded), normal shoulder joint function can become compromised. Typically, in these cases a surgical intervention can comprise a RSA procedure. Indeed, a TSA might not be indicated as normal operation of rotator cuff 74 can become compromised, thereby affecting the patient's ability to keep humeral head 72 within socket 71 of glenoid 70. In other words, since rotator cuff 74 is not functioning correctly, humeral head 72 can become dislodged from glenoid 70 during normal motion, leading a surgeon to perform a RSA.

Figure 2:
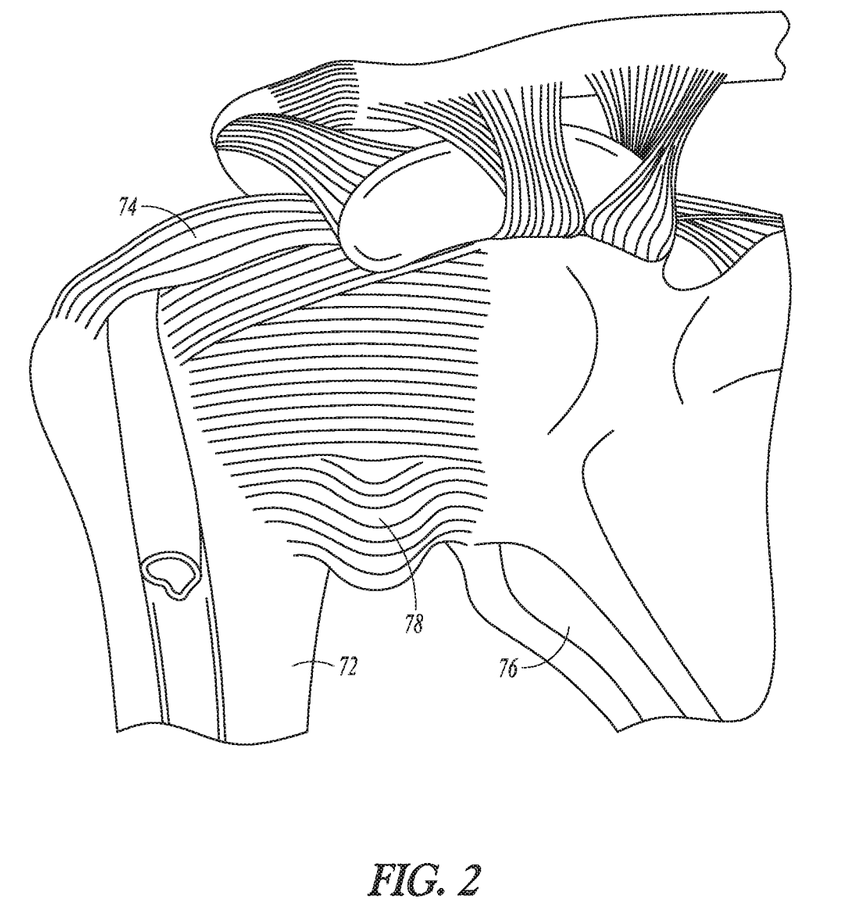

FIG. 2 illustrates the shoulder joint with its various ligaments intact. As is apparent, the joint includes a joint capsule 78, which comprises the glenohumeral ligaments. Joint capsule 78 can form a sac that surrounds humeral head 73 and glenoid 70, which acts to further stabilize the shoulder and allow for proper articulation of humeral head 73 within socket 71 without dislocation or other abnormalities occurring. In addition, rotator cuff 74 is shown in FIG. 2. Joint capsule 78 can attach to the margins of humeral head 73 and glenoid 70.

FIGS. 3A-5 illustrate a joint replacement 8, according to an example of the disclosure. Joint replacement 8 can include a humeral component 10 and/or a glenoid component 30. Joint replacement 8 can be a TSA replacement whereby humeral component 10 replaces a patient's humeral head 73 and glenoid component 30 replaces or augments a patient's glenoid 70. As such, glenoid component 30 can have a concave articulating surface that articulates and mates with a convex articulating surface of the head of humeral component 10. In other words, humeral component 10 can have a convex head that articulates with concave glenoid component 30, once implanted. Glenoid component 30 can also have one (1) or more openings for receiving fixation members (e.g., bone screws) used to attach glenoid component 30 to a patient's resected glenoid 70. Likewise, humeral component 10 can have a stem that can be inserted into the patient's humerus 72 and attached to the head of component 10.

Figure 3A:
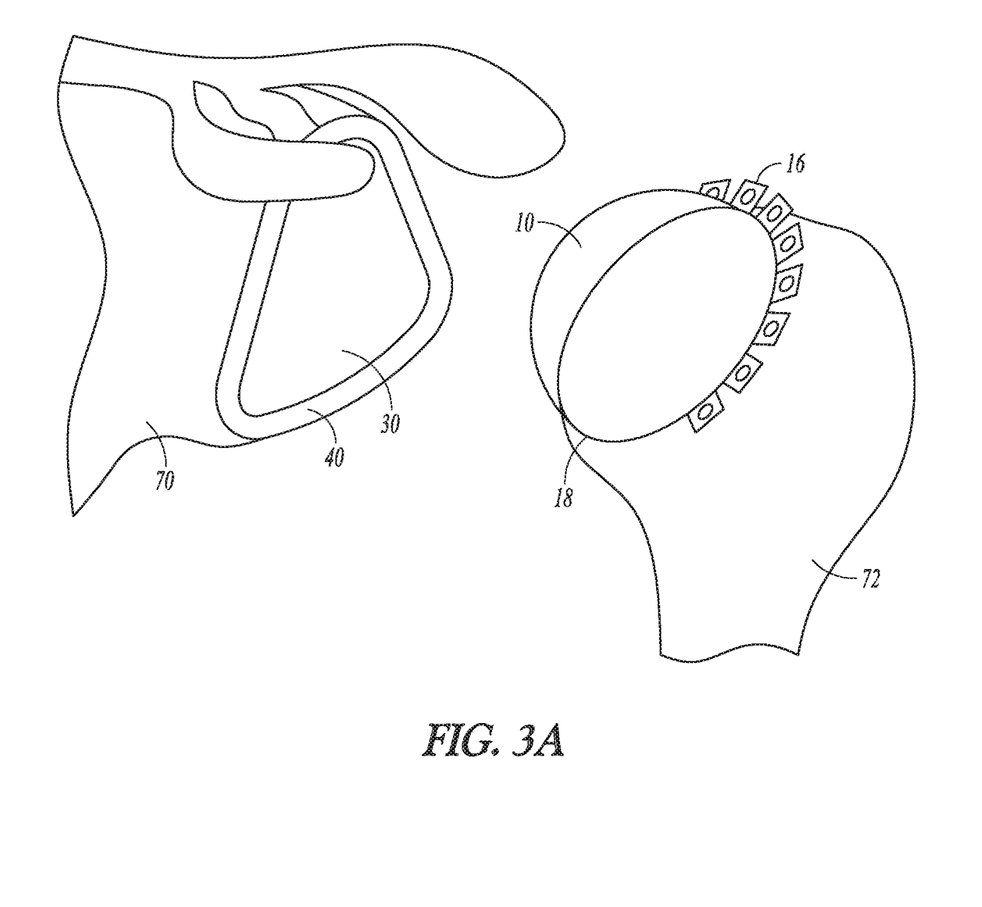
FIG. 3A is a perspective view of a joint replacement, according to an example of the disclosure without connecting bands.
Figure 3B:
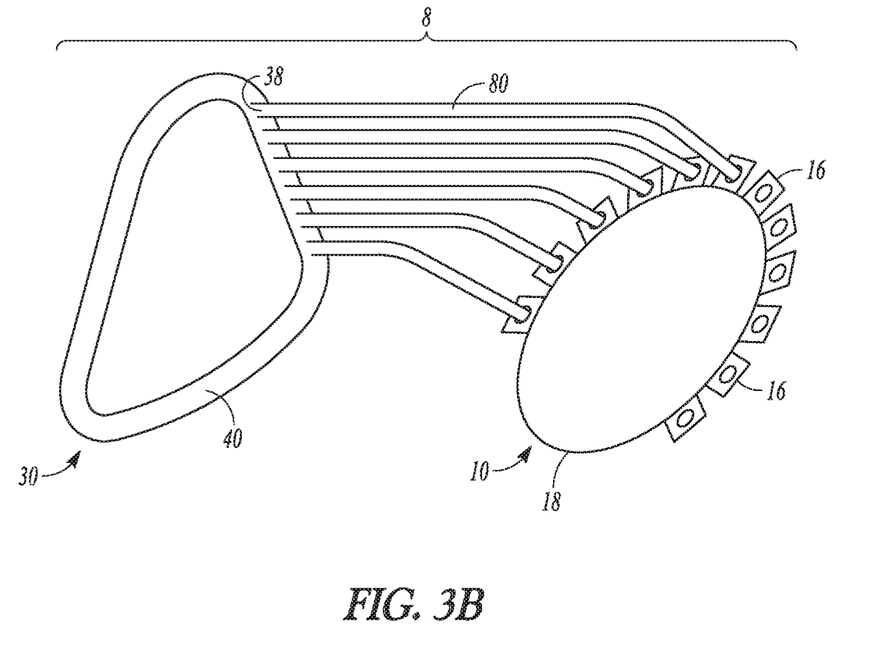
FIG. 3B is a perspective view of the joint replacement of FIG. 3A separated from anatomic structures and with connecting bands.
Figure 4:
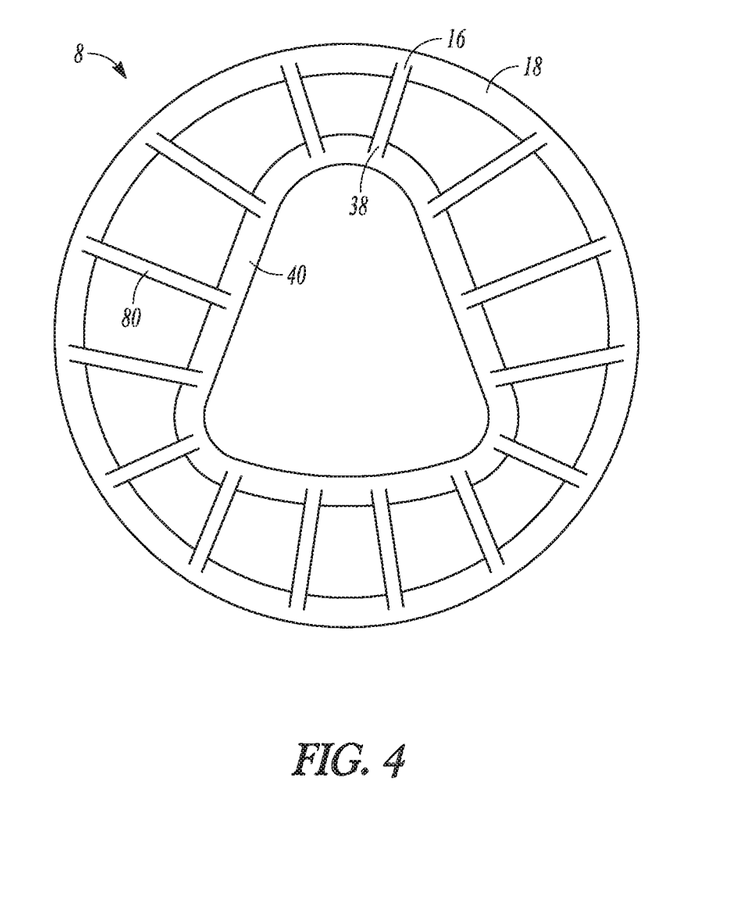
FIG. 4 is an end view of the joint replacement of FIGS. 3A-B.

As shown in FIGS. 3A-B, humeral component 10 can have a ring 18, which can include one or more attachment points 16 for bands 80 that can act to replace and/or augment natural ligaments of the patient's shoulder joint. In an example, ring 18 can extend partly or entirely around or adjacent a circumference of the head of humeral component 10. In addition, attachment points 16 can be positioned along part or all of ring 18, as explained in more detail below. In an example, attachment points 16 can be: (i) individual spaced-apart openings through ring 18 for accepting one or more bands 80, (ii) a slot or multiple slots in ring 18 for accepting one or more bands 80, or for accepting a prefabricated strip or component that is itself attached to a plurality of bands 80, (iii) an eyelet or series of eyelets sized to receive one or more bands 80, etc. Attachment points 16 can serve to capture a portion of bands 80 or another component connected to bands 80 so that bands 80 are firmly attached to ring 18, and thus humeral component 10. In an example, ring 18 can be a separate component that is attached to humeral component 10, or it can be formed into humeral component 10 itself. For instance, ring 18 can be co-molded with humeral component 10, or it can be a separate component that snap-fits or otherwise attaches to humeral component 10.

Referring to FIGS. 3A-5, glenoid component 30 can also include a ring 40, which can include one or more attachment points 38. As with above, attachment points 38 can engage with bands 80, which act to replace and/or augment natural ligaments of the shoulder joint. In an example, ring 40 can extend partly or entirely around or adjacent a circumference of the convex articulating surface of glenoid component 30. In addition, attachment points 38 can be positioned along part or all of ring 40, as detailed more fully below. In an example, attachment points 38 can be: (i) individual spaced-apart openings through ring 40 for accepting one or more bands 80, (ii) a slot or multiple slots in ring 40 for accepting one or more bands 80, or for accepting a pre-fabricated strip or component that is itself attached to a plurality of bands 80, (iii) an eyelet or series of eyelets sized to receive one or more bands 80, etc. Attachment points 38 can serve to capture a portion of bands 80 or another component connected to bands 80 so that bands 80 are firmly attached to ring 40, and thus glenoid component 30. In an example, ring 40 can be a separate component that is attached to glenoid component 30, or it can be formed into glenoid component 30 itself. For instance, ring 40 can be co-molded with glenoid component 30, or it can be a separate component that snap-fits or otherwise attaches to glenoid component 30.

Bands 80 can take a number of forms. As an example, bands 80 can be suture strands individually extending from glenoid component 30 to humeral component 10, suture braids, individual suture strands intermeshed into a mesh structure that extends from glenoid component 30 to humeral component 10, another mesh structure composed of any suitable flexible material (e.g., metal, a polymer, etc.), or any combination of the foregoing. As detailed below in connection with the surgical method, bands 80 can act to provide support for joint replacement 8 once it is implanted within the patient. Bands 80 can also include self-locking and/or adjustable loop sections (not shown), one (1) or more knots, or other suitable connection mechanisms for engaging with attachment points 16, 38. An example of a self-locking and/or adjustable loop suture is disclosed in U.S. Patent Pub. No. 2014/0330311, the disclosure of which is incorporated by reference herein in its entirety. Another example of a self-locking and/or adjustable loop suture is exemplified in Applicant's ZipLoop Technology.

An exemplary surgical method of using joint replacement 8 is now described. In an example, joint replacement 8 can be used in circumstances where a RSA is indicated. For instance, a patient might have a degraded or malfunctioning rotator cuff 74 and/or other ligament, which would normally preclude a TSA. However, due to the construction of joint replacement 8, joint replacement 8 can be used in a TSA and reestablish normal functioning of the patient's shoulder.

Figure 5:
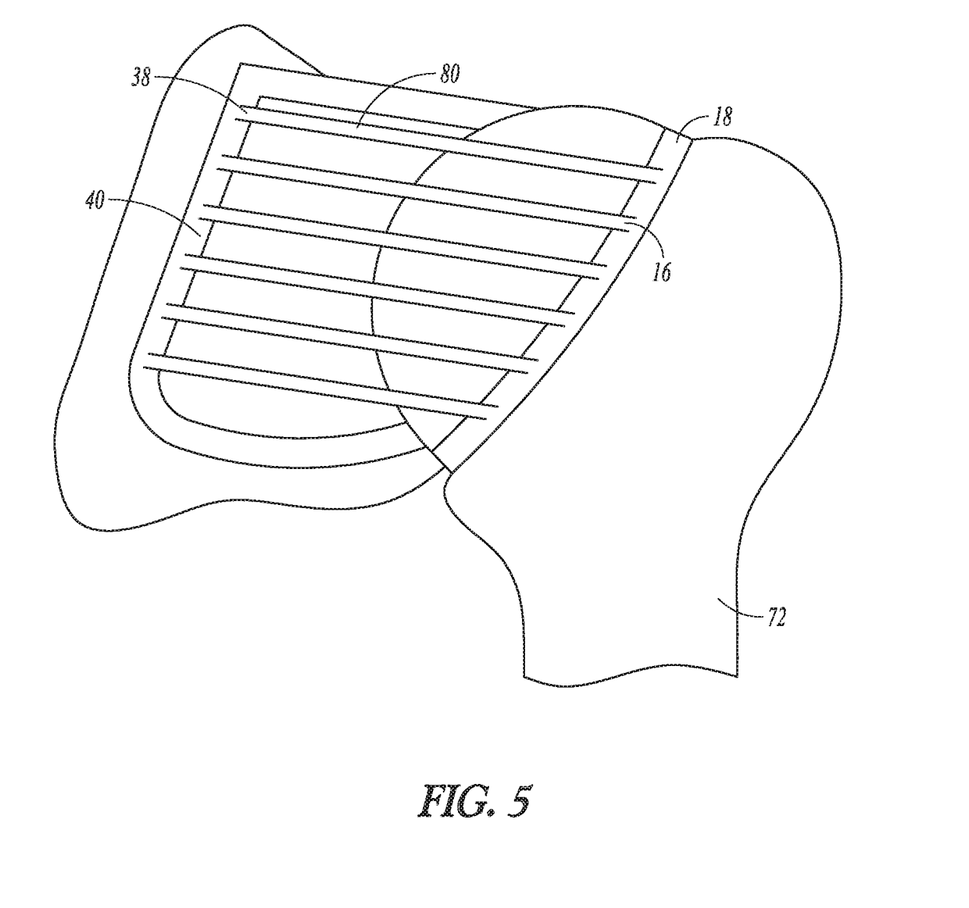
FIG. 5 is a side view of a joint replacement, according to an example of the disclosure, with the joint replacement attached to a patient's glenoid and humerus.

In the procedure, glenoid component 30 can be attached to the patient's glenoid 70, which can be resected or cut to receive component 30, as necessary. Glenoid component 30 can be attached to glenoid 70 so that its concave articulating surface is presented for articulation and mating with the head of humeral component 10. Humeral component 10 can be attached to the patient's humerus 72, for example by inserting the stem of humeral component 10 into humerus 72 and leaving the head of component 10 exposed for articulation with glenoid component 30.

Further, to restore normal shoulder function, bands 80 can engage with and/or link humeral and glenoid components 10, 30, and also provide tension and/or constraint between components 10, 30 to keep components 10, 30 engaged during normal shoulder movement. In other words, as detailed below, bands 80 can keep humeral component 10 closely engaged with glenoid component 30 during normal shoulder function since bands 80 can have a fixed length and/or be locked to prevent, for example, the head of humeral component 10 from moving out of the concave articulating surface of glenoid component 30.

Bands 80 can be separate from humeral component 10 and/or glenoid component 30 and then attach to such components 10, 30 during the surgical procedure, or bands 80 can be pre-attached to one or both of humeral components 10, 30. In an example, after attaching humeral component 10 and glenoid component 30 to humerus 72 and glenoid 70, respectively, ring 18 can be attached to humeral component 10 and ring 40 can be attached to glenoid component 30. In an alternative example, one or both rings 18, 40, with or without bands 80 pre-attached, can already be attached to humeral component 10 and glenoid component 30. In even further examples, as discussed with reference to alternative embodiments below, one or both rings 18, 40 can be omitted and attachment points 16, 38 can be formed on humeral component 10 (e.g., its head or a peripheral part thereof) and glenoid component 30 (e.g., a peripheral part of its concave articulating surface).

With rings 18, 40 attached to components 10, 30, bands 80 can be engaged with attachment points 16, 38 and tensioned to establish appropriate tension between humeral component 10 and glenoid component 30. In an example, bands 80 can be attached to rings 18, 40 through any of the mechanisms disclosed above. For instance, bands 80 can be composed of suture material, in individual strands or in mesh form, that can be looped through attachment points 16, 38 in the form of one or more openings, eyelets, or slots. Alternatively, attachment points 16, 38 can take the form of a slot, and a strip having one or more bands 80 attached thereto can be slid into the slot, such that the one or more bands 80 can be attached to rings 18, 40. In another example, a metal mesh or a mesh composed of non-suture material can be used as bands 80 and can be attached to attachment points 16, 38.

With bands 80 attached to rings 18, 40, one or more bands 80 can be tensioned to establish appropriate tension between humeral component 10 and glenoid component 30. In an example, suitable tensioning mechanisms can include bands 80 having adjustable suture loops with locking structures (e.g., self-locking passages, slip knots, etc.), for example similar to as disclosed in '311 Publication, incorporated by reference above. If a mesh is used as bands 80, the mesh can include an adjustable portion that acts to tension the mesh to an appropriate tension. If there is any excess material after tensioning of bands 80, it can be cut away and discarded. In addition, as noted above, bands 80 can include a locking structure (e.g., self-locking suture) that acts to lock bands 80 in their tensioned state after tensioning.

Bands 80 can be placed around part or the entirety of rings 18, 40, ring 18 can extend around or adjacent to part or all of the circumference of the head of humeral component 10, and ring 40 can extend around or adjacent to part or all of the circumference of the concave articulating surface of glenoid component 30. A surgeon can choose to place bands 80 along a certain location or segment of rings 18, 40 to provide tension and/or constraint in that area, while leaving other areas of rings 18, 40 without bands 80. Likewise, rings 18, 40 can be formed along only certain areas or segments of humeral component 10 and/or glenoid component 30 for the same reason. In even further examples, the surgeon can choose to tension certain bands 80 in certain areas more or less than other bands 80. A surgeon may choose to tension certain bands 80 differently to apply an appropriate amount of tension to the shoulder joint via joint replacement 8, which replicates the normal tension that might be present if the relevant ligament(s) or tissue(s) were functioning effectively. For instance, bands 80 might be tensioned to a certain threshold and/or placed along a certain segment of rings 18, 40 to replicate the normal function of rotator cuff 74. As such, bands 80 can act to ensure that the head of humeral component 10 remains mated with the concave articulating surface of glenoid component 30 during use. Joint replacement 8 can therefore be used in circumstances where a RSA would normally be indicated (e.g., compromised rotator cuff 74 and/or other ligaments). Stated differently, joint replacement 8 can provide stabilization to the patient's shoulder in instances where the patient's ligaments might be damaged or degraded. Thus, joint replacement 8 can be used in circumstances where a RSA normally would be used.

Alternative examples of joint replacement 8 can also be utilized to achieve similar goals to those set forth in the present disclosure. For instance, it is contemplated that one or more of rings 18, 40 can be omitted, and that certain attachment points 16, 38 might be formed in bone. In an example, certain attachment points 16, 38 could be formed as suture holes in the native humerus 72 and/or glenoid 70.

In a further example, a mesh structure is disclosed above as an exemplary band 80. The mesh structure could be used to substantially completely surround glenoid 70 and/or humerus 72 and provide a synthetic joint capsule. The mesh structure can be tighter in certain areas and looser in other areas to provide for the appropriate tension needed for the patient's shoulder joint.

In yet another example, bands 80 can be placed along a certain section of rings 18, 40 and/or at certain attachment points 16, 38 and not in other areas. This can be useful in situations where the particular patient might be susceptible to a certain type of dislocation (e.g., posterior) and a surgeon wishes to prevent such a dislocation using joint replacement 8 and its bands 80.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. A joint replacement system comprising: a glenoid component including a concave articulating surface and a peripheral surface; a humeral component including a convex head and a peripheral surface; and a first flexible band attached to the peripheral surfaces of the glenoid component and the humeral component, the first flexible band linking the glenoid component to the humeral component and providing tension therebetween; further comprising a first opening on the peripheral surface of the glenoid component, wherein a portion of the first flexible band is inserted through the first opening to attach the first flexible band to the peripheral surface of the glenoid component, and a first opening on the peripheral surface of the humeral component, wherein a portion of the first flexible band is inserted through the first opening to attach the first flexible band to the peripheral surface of the humeral component.

2. The joint replacement system of claim 1, further comprising a plurality of flexible bands attached to the peripheral surfaces of the glenoid component and the humeral component, the plurality of flexible bands linking the glenoid component to the humeral component and providing tension therebetween.

3. The joint replacement system of claim 1, wherein the first flexible band is composed of suture.

4. The joint replacement system of claim 1, further comprising a second flexible band attached to the peripheral surfaces of the glenoid component and the humeral component, the second flexible band linking the glenoid component to the humeral component and providing tension therebetween, where the second flexible band is tensioned tighter than the first flexible band.

5. The joint replacement system of claim 1, further comprising a mesh linking the glenoid component to the humeral component.

6. The joint replacement system of claim 5, wherein the first flexible band is part of the mesh.

7. The joint replacement system of claim 1, wherein the first flexible band has a self-locking structure.

8. A method of implanting a joint replacement comprising: attaching a glenoid component to a patient's glenoid; attaching a humeral component to a patient's humerus; inserting a portion of a first flexible band to the peripheral surface of the glenoid component, inserting a portion of the first flexible band through a first opening on a peripheral surface of the humeral component to attach the first flexible band to the peripheral surface of the humeral component; and tensioning the first flexible band to keep the patient's humeral component in registration with the glenoid component.

9. The method of claim 8, further comprising linking the glenoid component to the humeral component using a plurality of flexible bands.

10. The method of claim 9, wherein the plurality of flexible bands comprise a mesh that links the glenoid component to the humeral component.

11. The method of claim 8, further comprising linking the glenoid component to the humeral component using a second flexible band, and tensioning the second flexible band to a greater degree of tension than the first flexible band.

12. The method of claim 8, further comprising locking the first flexible band after tensioning the first flexible band.

13. The method of claim 12, wherein the first flexible band comprises a self-locking mechanism, and the method further comprises self-locking the first flexible band after tensioning the first flexible band.

14. The method of claim 13, wherein first flexible band is composed of suture, and the self-locking mechanism comprises a self-constricting passage formed in the suture.

15. The method of claim 14, further comprising passing a portion of the first flexible band through the self-constricting passage to form a loop of suture.

16. The method of claim 15, further comprising pulling on a free end of the first flexible band to decrease a size of the loop of suture, thereby causing the self-constricting passage to constrict about the portion of the first flexible band and lock the first flexible band within the self-constricting passage.

* * * * *

UNITED STATES PATENT AND TRADEMARK OFFICE
CERTIFICATE OF CORRECTION

Page 1 of 1

PATENT NO. : 10,582,999 B2
APPLICATION NO. : 16/028802
DATED : March 10, 2020
INVENTOR(S) : Michael Francis Kovacs It is certified that error appears in the above-identified patent and that said Letters Patent is hereby corrected as shown below:

In the Claims

In Column 7, Line 59, in Claim 1, after "comprising:", insert --¶--

In Column 7, Line 61, in Claim 1, after "surface;", insert --¶--

In Column 7, Line 62, in Claim 1, after "and", insert --¶--

In Column 8, Lines 31-32, in Claim 8, after "comprising:", insert --¶--

In Column 8, Line 32, in Claim 8, after "glenoid;", insert --¶--

In Column 8, Line 33, in Claim 8, after "humerus;", insert --¶--

In Column 8, Line 34, in Claim 8, after "band", insert --through a first opening on a peripheral surface of the glenoid component to attach the first flexible band--

Signed and Sealed this
Tenth Day of November, 2020

Andrei Iancu
*Director of the United States Patent and Trademark Office*